United States Patent [19]

Pomeranz et al.

[11] Patent Number: 4,556,064
[45] Date of Patent: Dec. 3, 1985

[54] ELECTROTHERAPY ACUPUNCTURE APPARATUS AND METHOD

[76] Inventors: Bruce Pomeranz, 25 Governor's Rd., Rosedale, Ontario, Canada, M4W 2E9; Norman Salansky, 6 Hearthstone Crescent, Willowdale, Ontario, Canada, M2R 1G3

[21] Appl. No.: 460,969

[22] Filed: Jan. 25, 1983

[51] Int. Cl.$^4$ .............................................. A61N 1/36
[52] U.S. Cl. .................................. 128/423 R; 128/395
[58] Field of Search ................ 128/329 A, 420 R, 421, 128/422, 423 R, 395

[56] References Cited

U.S. PATENT DOCUMENTS

| | | | |
|---|---|---|---|
| 3,077,884 | 2/1963 | Batrow et al. | 128/423 R |
| 3,897,789 | 8/1975 | Blanchard | 128/422 |
| 3,900,020 | 8/1975 | Lock | 128/422 |
| 3,901,247 | 8/1975 | Walmsley | 128/422 |
| 3,902,502 | 9/1975 | Liss et al. | 128/422 |
| 3,946,745 | 3/1976 | Hsiang-Lai et al. | 128/421 |
| 4,153,059 | 5/1979 | Fravel et al. | 128/422 |

OTHER PUBLICATIONS

Pettijohn, "Behavior Research Methods + Instrumentation", vol. 8, No. 3, Jun. 1976, pp. 287-289.

Primary Examiner—William E. Kamm
Attorney, Agent, or Firm—Rogers, Bereskin & Parr

[57] ABSTRACT

A circuit for electrotherapy and electronic acupuncture, in which a pulse train is produced having negative pulses of a repetition rate of between 100 and 500 Hz, arranged in groups having a repetition rate of between 1 and 50 Hz. A positive bias is provided so that the integral of the pulse train signal is zero. The signal is randomly switched sequentially from one skin stimulus site to another with application times which can be adjusted between about 1 and 20 seconds (or more), to reduce or prevent brain habituation. Optionally there is a rest period between applications of the signal, in which no signal is applied to the skin sites.

28 Claims, 15 Drawing Figures

ELECTROTHERAPY ACUPUNCTURE APPARATUS AND METHOD

This invention relates to a method and apparatus for use in electrotherapy, particularly in electronic acupuncture. The method and apparatus of the invention may also be used for applying other stimulating signals to a user.

Acupuncture has been practiced for many centuries in China but has been adopted only to a very modest extent in the West. A major deterrent has been that acupuncture has traditionally typically required a one hour treatment per day by a physician over several months, employing needles. Many patients have a fear or dislike of needles and the amount of physicians' time required per patient is too high.

To avoid the use of needles, transcutaneous electro acupuncture instruments employing hand held pencil shaped probes have been developed, as disclosed in U.S. Pat. No. 4,180,079 issued Dec. 25, 1979 to T. W. Wing. Such instruments have relied upon the application of electrical pulses instead of needles. They have not so far as the applicants are aware been successful and have not been widely used.

The invention in one of its aspects provides a device which can be used to provide daily acupuncture treatment at a clinic or a user's homes without the use of needles or probes. According to the invention in one aspect, at least three acupuncture points on the user's body are selected and electrode pads are secured to the skin surface at these points. Electrical pulses are then applied to one or more of these points at a time and are randomly switched among the points to prevent habituation of the nervous system to repetitive signals.

In one aspect the invention provides apparatus for applying a stimulating signal to a user comprising:

(a) means for providing said stimulating signal, (b) at least three channels each for applying said signal to said user, (c) and means for randomly switching said signal among said channels to reduce habituation of the brain of said user.

In another aspect the invention provides acupuncture apparatus comprising:

(a) means for producing an electrical acupuncture signal, (b) at least three channels each for applying said signal to a user, (c) and means for randomly switching said signal among said channels to reduce habituation of the brain of said user.

In another aspect the invention provides electro-stimulation apparatus comprising:

(a) means for providing a transcutaneous nerve stimulation signal, (b) at least three channels each for applying said signal to a user, (c) and means for randomly switching said signal among said channels to reduce habituation of the brain of said user.

In still another aspect the invention provides acupuncture apparatus comprising:

(a) means for providing an electrical acupuncture signal, (b) at least three channels each for applying said signal to a user, (c) and a set of electroconductive pads, one pad for each channel, each pad being of area at least equal to one square centimeter and including fastening means secured thereto for securing such pad firmly over an acupuncture point.

Further objects and advantages of the invention will appear from the following description, taken together with the accompanying drawings in which.

Figure 1:
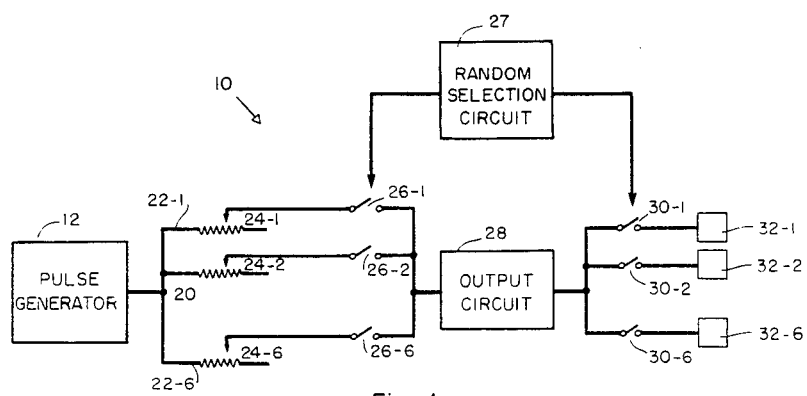
FIG. 1 is a block diagram of apparatus according to the present invention.
Figure 2:
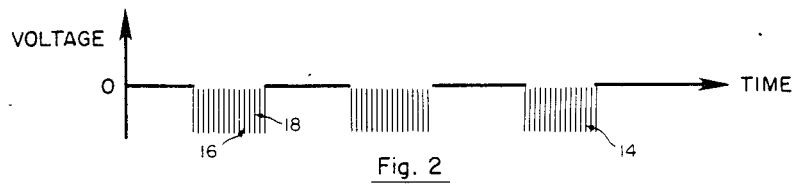
FIG. 2 shows a pulse train produced by the apparatus of FIG. 1.

Reference is first made to FIG. 1, which shows a block diagram of an electrotherapy (e.g. electronic acupuncture) apparatus 10 according to the invention. As shown, the apparatus 10 includes a pulse generator 12 which produces a pulse train of the kind shown at 14 in FIG. 2. The pulse train 14 consists of a set of negative pulses 16 of repetition rate equal approximately to 200 Hz, divided into groups 18 having a repetition rate of approximately 4 Hz. In practice, the optimum frequencies can differ from one individual to another and therefore the repetition rate of pulses 16 can be made adjustable from about 100 to 500 Hz and the repetition rate of the groups 18 of the pulses 16 can be made adjustable from about 1 to 50 Hz.

It has been determined in accordance with the invention that the stimulation of more than one acupuncture point at the same time or in reasonably close time proximity is much more effective than the stimulation of a single acupuncture point. It appears that the stimulation of more than one point at a time or in reasonably close time proximity causes a synergistic effect. Therefore the pulse train generator output terminal, indicated at 20, is connected to a number of channels (here shown as six in number) identified by conductors 22-1 to 22-6 in FIG. 1. The conductors 22-1 to 22-6 are directed to six separate gain controls 24-1 to 24-6 so that the gain of each channel can be separately adjusted, thus to control the intensity of the signal applied to the subject through each channel. A seventh channel, not shown, is neutral.

It has been determined in accordance with the invention that if an electronic acupuncture signal is applied to any acupuncture point for a long period of time, the brain habituates, i.e. it tends to filter out any such monotonous signal. Depending on the individual, it is found that the brain commonly habituates in between about 2 and 20 seconds. Therefore, according to the invention the electronic acupuncture signal (i.e. the pulse train 14 shown in FIG. 2) is switched randomly from one channel to another to prevent or reduce habituation. (The randomness bypasses the brain filters and dishabituates the neural circuits.)

Accordingly, the outputs of the gain controls 24-1 to 24-6 are directed through a set of six channel select switches 26-1 to 26-6. The switches 26-1 to 26-6 are closed one at a time in random sequence by a random selection circuit 27, to be described. The outputs of the channel select switches are connected together and directed to a single output circuit 28 which sets the output current and also acts as a constant current source. The constant current source output circuit is used to overcome variations in skin impedance during treatment and to maintain a steady current during treatment.

The output of output circuit 28 is fed through another set of six channel select switches 30-1 to 30-6. Switches 30-1 to 30-6 are formed by relay contacts of relays (to be described) which are ganged with channel select switches 26-1 to 26-6 so that they are operated, one at a time, in unison with switches 26-1 to 26-6. The switches 30-1 to 30-6 are to ensure complete disconnection of any electrical circuit from a skin pad except when the relay in question is closed. The switches 30-1 to 30-6 are directed to six pads 32-1 to 32-6 which are in use secured to acupuncture points at six different locations on a user's body.

Figure 3:
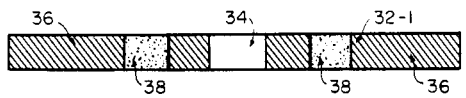
FIG. 3 shows a skin pad and tape arrangement for use with the apparatus of the invention.

A typical pad 32-1 is shown diagrammatically in FIG. 3 (all are the same). The pad 32-1 consists of an electroconductive surface larger than one $cm^2$ surface area (e.g. standard carbon impregnated polymer pad 34) secured to the skin by a band 36, or any adhesive tape which can stick to the skin. The band 36 may have plastic portions 38 spliced therein or be of elastic material throughout so that when the pad is applied over an acupuncture point and the band is used to secure the pad in position, sufficient tension can be achieved to press the pad firmly against the user's skin. The band can be buckled by Velcro (trade mark) tape. As the pads are larger than one $cm^2$, the likelihood of missing the acupuncture points is greatly reduced. Hence less skill is required for a patient to self administer the pads.

Figure 4:
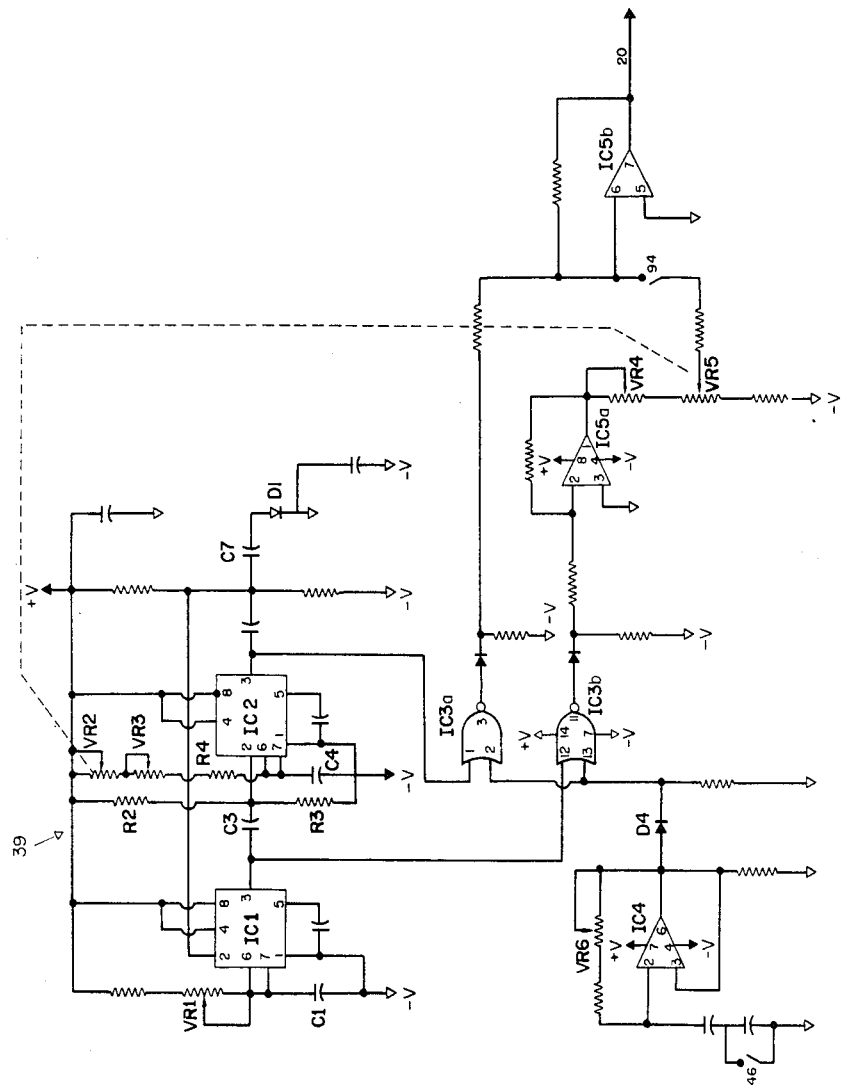
FIG. 4 is a circuit diagram showing in detail the pulse generator of the FIG. 1 apparatus.

A detailed explanation of the circuit shown in FIG. 1 now follows, with reference firstly to FIG. 4, which shows the pulse generator circuit 12 in detail. As shown, the pulse generator circuit 12 includes two model ICM 555 integrated circuits made by Intersil Inc. of Cupertino, Calif., U.S.A. and indicated at IC1 and IC2. The numbers shown in brackets on the integrated circuits (and on the other integrated circuits shown in the drawings) are the actual pin numbers of the devices as sold. The integrated circuits IC1 and IC2 are connected in standard fashion to form a variable duty cycle multi-vibrator 39 which is best understood from a description of its operation, which is as follows. When power is applied, by a switch not shown, capacitor C7 charges via diode D1, briefly holding pin 2 of circuit IC1 low. This triggers circuit IC1 whose output pin 3 goes high.

The period for which circuit IC1 remains on is determined by the voltage at its pins 6 and 7. When capacitor C1 charges through resistors R1 and VR1 to a predetermined level, circuit IC1 goes off. The duration of the on cycle of circuit IC1 is typically set at one millisecond (but can be varied from 50 microseconds to one millisecond) by adjustment of resistor VR1. Variations in the duration of the pulses produces a significant change in the effect of the pulses on the user. Since longer pulses produce stimulae of greater intensity, this provides a second adjustment (common to all channels) of the intensity of the stimulae applied to the user (the first adjustment being the gain control resistors 24-1 to 24-6 for the individual channels as mentioned).

When circuit IC1 turns off, its pin 3 goes low and triggers circuit IC2 via capacitor C3 and resistors R2, R3. Circuit IC2 turns on and its pin 3 goes high for a period determined by the voltage at its pins 6 and 7, controlled by capacitor C4 charging through resistors VR2, VR3, R4. With variable resistor VR2 set at zero resistance, variable resistor VR3 is adjusted so that the on cycle of circuit IC2 is 1.5 milli-seconds. Capacitor C4 is selected such that when variable resistor VR2 is adjusted from zero to 50,000 ohms, the on period of circuit IC2 changes from 1.5 milliseconds to 9 milliseconds.

The outputs from pins 3 on circuits IC1 and IC2, shown at 40 and 42 in FIG. 5a and FIG. 5b, are fed respectively to integrated circuits IC3b and IC3a, which together form a quad NOR gate. Both circuits IC3a and IC3b are formed on a single chip sold under No. CD4001 by the RCA company of New Jersey, U.S.A.

Circuits IC3a and IC3b are also controlled by an oscillator IC4. Oscillator IC4, which consists of an integrated circuit sold under No. TL081 by Texas Instruments of Dallas, Tex., U.S.A. is connected in standard oscillator configuration to produce pulses as shown at 44 in FIG. 5c.

The frequency of oscillator IC4 is adjusted by variable resistor VR6, and the range of frequencies is adjusted by switch 46. In the open position shown, the repetition rate of oscillator IC4 is adjustable from one to ten Hz, while when switch 46 is closed, the repetition rate of oscillator IC4 is adjustable from 5 to 50 Hz.

The output from oscillator IC4 is used to gate the pulses from circuits IC2 and IC3. When the output from oscillator IC4 is positive, diode D4 conducts and drives pins 2 and 13 of circuits IC3a, IC3b high. This holds the outputs of these circuits low, inhibiting pulse output. When the output of oscillator IC4 goes negative, diode D4 is reverse biased; pins 12 and 13 on circuits IC3a, IC3b go low, and pulses appear at the outputs of these circuits.

It will be seen that because an output is produced by circuit IC3b only when the outputs of oscillator IC4 and circuit IC1 are both low, thus the output from gate IC3b coincides in time with the times when circuit IC2 is on. Similarly, because there is an output from circuit IC3a only when the outputs of oscillator IC4 and circuit IC2 are both low, thus the output from gate IC3a coincides with the times when circuit IC1 is on. The output pulses from circuits IC3a and IC3b are shown at 48, 50, respectively in FIG. 5d and 5e.

The pulses 48 from circuit IC3b are directed to pin 2 of integrated circuit IC5a, which is formed by an integrated circuit sold under No. LF353 by National Semiconductor of California, U.S.A. Circuit IC5a inverts the pulses 48 and feeds the inverted pulses via its output pin 1 to a potential divider consisting of variable resistors VR4 and VR5. Variable resistor VR5 is ganged as shown to variable resistor VR2 and in fact the two resistors are formed by a dual 50,000 ohm control, for a purpose to be described shortly.

The output from variable resistor VR5, shown at 52 in FIG. 5f, is combined with the output from circuit IC3a in an adder IC5b. Adder IC5b is an integrated circuit formed on the same chip as circuit IC5a. The polarity of the resultant signal is inverted in adder IC5b, so that the output pulse train now appears as shown at 14 in FIG. 5g and is in fact the final pulse train, subject to processing through a constant current source.

The purpose of the ganged resistors VR2 and VR5 is as follows. It is found that if only negative pulses are applied to tissue during electronic acupuncture, the points of application become polarized and the application of the pulses becomes less effective. The circuits shown ensures that the integral of the output signal 14 from circuit IC5b is always zero, i.e. that the area under the positive bias pulses 14b is always equal to the area under the negative or stimulating pulses 14a.

In order to ensure that the integral of signal 14 is zero, the relation $A_{14a}T_{14a}=A_{14b}T_{14b}$ must be maintained, where $A_{14a}$ is the amplitude of pulses 14a; $T_{14a}$ is the duration of each pulse 14a; $A_{14b}$ is the amplitude of the bias pulses 14b; and $T_{14b}$ is the duration of each bias pulse 14b.

Since in the initial setting the duration of the stimulating pulses $T_{14a}$ is set at 1 millisecond and the duration of the bias pulses $T_{14b}$ is set at 1.5 milliseconds, therefore variable resistor VR4 is initially adjusted so that $A_{14b}=\frac{2}{3}A_{14a}$. Then, as variable resistor VR2 is adjusted to vary the period between pulses 14a (i.e. the length of the bias pulses 14b) from 1.5 to 9 milliseconds, the amplitude $A_{14b}$ of the bias pulses is adjusted automatically to vary from $\frac{2}{3}$ to 1/9 of $A_{14a}$.

Figure 6:
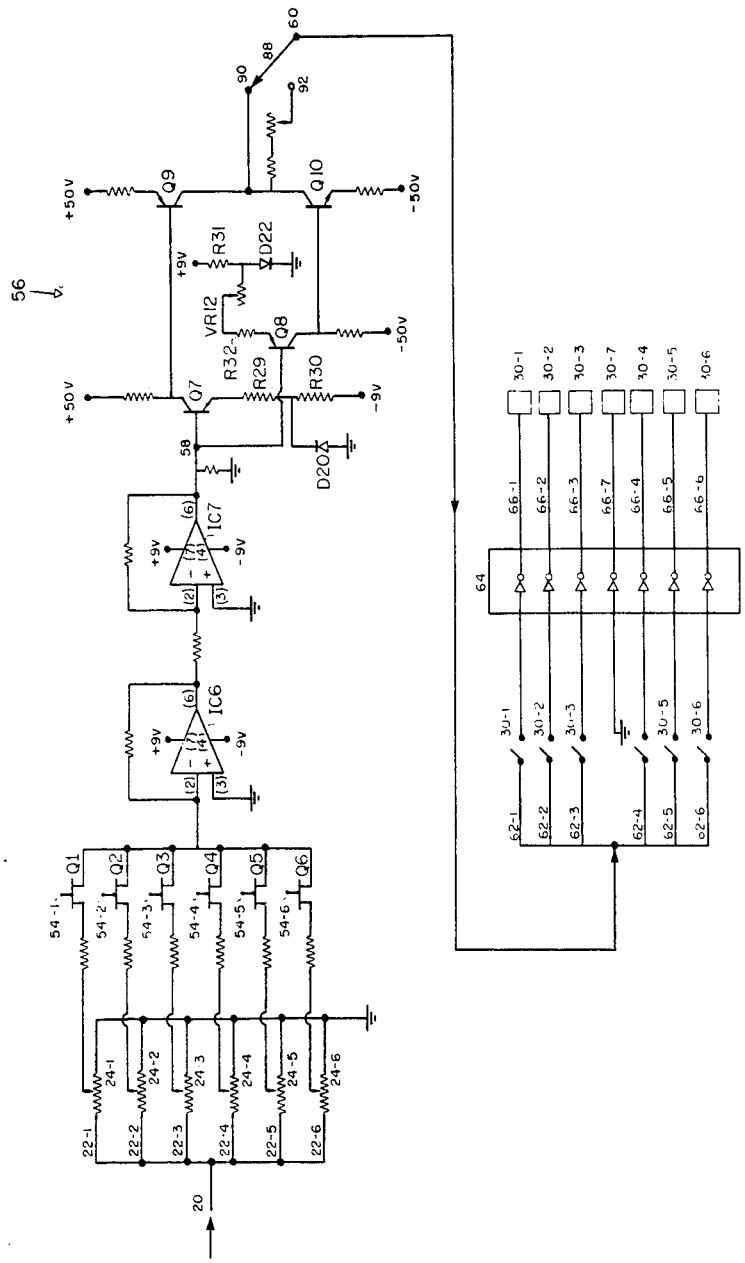
FIG. 6 is a circuit diagram showing in detail other portions of the FIG. 1 apparatus.

The final pulse train 14 from circuit IC5b is directed to the six channel conductors 22-1 to 22-6 and hence to the six gain controls 24-1 to 24-6 (FIG. 6). From the gain controls the pulse train or signal 14 is directed through the six channel select switches 26-1 to 26-6, here shown as six field effect transistors Q1 to Q6. The gates 54-1 to 54-6 of transistors Q1 to Q6 are connected to the random selection circuit 27 as will be described. The drains of transistors Q1 to Q6 are connected together and to an operational amplifier IC6 which provides gain and improvement of the pulse train shape. Since amplifier IC6 acts as an inverter, its output is again inverted by amplifier IC7 to present the correct polarity signal to the output circuit.

The output circuit is shown at 56 in FIG. 6 and includes four transistors Q7, Q8, Q9 and Q10. Bias networks D20, R29 and R30, and D22, D31, VR12 and R32 set the collector currents of transistors Q7 and Q8 at about 0.5 milliamperes. This in turn sets the collector currents of transistors Q9 and Q10 at about 2.8 milliamperes. A positive signal at the input 58 of the output circuit 56 turns transistor Q7 on and transistor Q8 off. A negative signal turns transistor Q7 off and transistor Q8 on. Thus, a positive signal has one channel through the output circuit to the load, and a negative signal has another channel through the output circuit to the load. The arrangement shown acts essentially as a constant current source, helping to ensure that the current applied to the load (i.e. to the skin pads 32-1 to 32-6) is constant despite changes in skin impedance and in the contact between the pads and the skin during treatment. In addition, variable resistor VR12 allows the output current to be set to zero (or to a small predetermined DC value, as will be explained) when there is no input signal to the output circuit 56. Circuit 56 is typically able to deliver negative pulses of between 50 and 5000 microamperes to the load.

The signal from the output terminal 60 of the output circuit 56 is directed through six conductors 62-1 to 62-6 (FIG. 6) and the six relay contacts 30-1 to 30-6 to an output connector 64. The output connector 64 is connected through six conductors 66-1 to 66-6 to the six skin pads 32-1 to 32-6. The conductors 66-1 to 66-6 are preferably colour coded for ease of identification by the user. A seventh conductor 66-7 acts as a common lead and is connected to ground in the apparatus 10 and to a seventh skin pad 32-7 which is connected at any desired location to the user.

Figure 7:
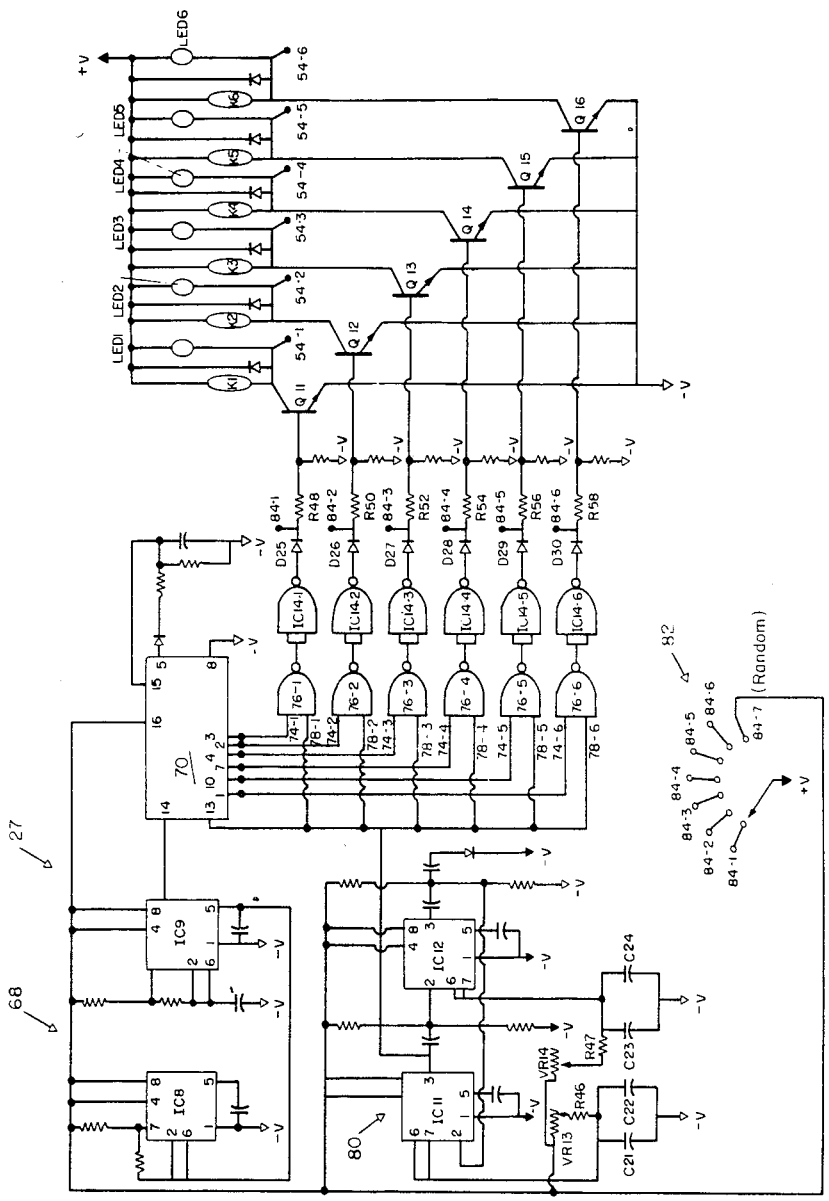
FIG. 7 is a circuit diagram showing in detail the random selection circuit of the FIG. 1 apparatus.
Figure 9:
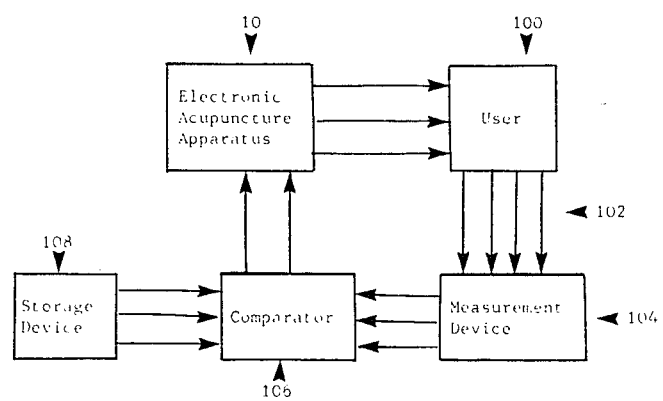
FIG. 9 is a block diagram of a biofeedback arrangement which may be used with the apparatus of the invention.

Reference is next made to FIG. 7, which shows the random selection circuit 27 which controls the channel selection transistors Q1 to Q6 and relay contacts 30-1 to 30-6. As shown, selection circuit 27 includes a variable frequency oscillator 68 formed by two integrated circuits IC8, IC9, both circuits sold under No. ICM 555 by Intersil Inc. of Cupertino, Calif., U.S.A. The circuits are connected as shown to form a variable frequency oscillator having a center frequency of about 800 Hz and a relatively rapid variation frequency about this center frequency. Specifically, circuit IC9 produces oscillations at a frequency of 800 Hz which are modulated by ±50 Hz by circuit IC8. A typical variation in frequency of oscillator 68 with time is shown at 69 in FIG. 8. In a prototype unit built according to the invention, the period or time required for the variation between 750 Hz and 850 Hz was 70 milliseconds.

The output pin 3 of circuit IC9 of oscillator 68 is connected to a counter 70. Counter 70 is typically model CD4017 sold by the RCA company of New Jersey, U.S.A. Counter 70 has six sequential outputs 72, also indicated by the pin numbers shown in brackets of the device as actually sold (1, 10, 7, 4, 2, 3). The variable frequency oscillator 68 drives the counter 70 at a count rate which varies with the frequency of oscillator 68. As the count proceeds, the six output pins 72 of the counter 70 are driven high in sequence. On the seventh count, pin 5 of counter IC10 goes high and resets the counter to zero.

The six output pins 72 of counter 70 are connected respectively to the inputs 74-1 to 76-1 of six NAND gates 76-1 to 76-6. The other six inputs of the NAND gates 78-1 to 78-6 are connected together and to the inhibit pin 13 of counter 70, as well as to the output of a multivibrator oscillator 80.

Multivibrator 80 is similar to the oscillator 39 shown in FIG. 4 and consists of two integrated circuits IC11 and IC12, both circuits model numbers ICM7555 connected as shown in a similar manner to that of FIG. 1. The "on" period of circuit IC11 is set by capacitors C21, C22 and resistors R46, VR13. The "off" time of circuit IC11, which is the "on" time of circuit IC12, is set by capacitors C23, C24 and resistors R47, VR14. The output pin 3 of circuit IC11 serves as the output of multivibrator 80 and is connected as mentioned to the inhibit pin 13 of counter 70 as well as to the six inputs 78-1 to 78-6 of NAND gates 76-1 to 76-6.

The outputs of NAND gates 76-1 to 76-6 are connected respectively to six inverters, shown as integrated circuits IC14-1 to IC14-6 (formed in pairs on three chips each model number CD4011 sold by the RCA company of New Jersey, U.S.A.). The inverter outputs are respectively connected through six diodes D25 to D30 and six resistors R48 to R58 to the bases of six transistors Q11 to Q16. Each transistor Q11 to Q16 has its collector connected to ground and its emitter connected to a respective relay coil K1 to K6, the other terminals of the relay coils being connected to +9 volts. The relay contacts 30-1 to 30-6 are contacts of relays K1 to K6 respectively. Each relay coil K1 to K6 has a light emitting diode LED-1 to LED-6 respectively connected across it to indicate when it is operated.

In addition, the collectors of transistors Q11 to Q16 are connected respectively to the gates 54-1 to 54-6 of field effect transistors Q1 to Q6 (FIG. 6).

The selection action of the random selection circuit 27 is as follows. Assume that counter 70 is counting and circuit IC11 is off. When circuit IC11 turns on, its pin 3 goes high; counter 70 is inhibited, stopping it in mid count, and one only of the NAND gates 76-1 to 76-6 (connected to the counter pin at which the count has stopped) will have both its inputs high. Assume that the selected gate is gate 76-4. The selected gate 76-4 will remain in this condition so long as circuit IC11 remains on, since continued counting of the counter 70 has been inhibited.

The selected NAND gate 76-4, having both its inputs high, has a low output which when fed through inverter IC14-4 produces a high output to transistor Q14. Transistor Q14 then turns on, operating relay K4 and turning on field effect transistor Q4. When relay K4 operates, its contact 30-4 closes. This causes the pulse train 14 to be applied through conductors 22-4, 62-4 and 66-4 to pad 32-4. At the same time, light emitting diode LED-4 glows, indicating that relay K-4 has been operated and that signal is being applied through pad 32-4 to the user.

When circuit IC11 turns off, the input 78-4 of selected NAND gate 76-4 goes low. Since one of the inputs to gate 76-4 is now low, the output of gate 76-4 goes high again, and the output of inverter IC15-4 goes low, cutting off current to the selected transistor Q14 and turning off relay K4. Hence no pulse train is applied to any of the pads until circuit IC11 turns again.

It will thus be seen that the application time of the pulse train 14 to each skin pad 32-1 to 32-4 is controlled by the on time of circuit IC11, and the rest period between applications of signal to a skin pad is controlled by the on time of circuit IC12. The on time of circuit IC11 can be adjusted by variable resistor VR13 as desired, typically between 2 and 20 seconds. The on time of circuit IC12 (i.e. the rest intervals between applications of the pulse train) can be controlled by adjustment of variable resistor VR15 and will typically be between 1 and 10 seconds.

Although the provision of a rest interval between application of pulse trains is not essential, it is found to be helpful both in providing relief between stimulations and in enhancing dishabituation of the brain.

Although it is preferred that a substantial number of pads at a number of acupuncture points be used at one time (e.g. at least five or six points), it is found that reasonable dishabituation of the brain can be achieved with randon switching between at least three points.

It should be noted that the term "random" as used in this description and in the appended claims is not intended to mean a truly random switching, since virtually any practical circuit used will have a pattern which will at some time repeat. However, the objective is simply to provide a switching pattern, from one pad to another, which is sufficiently variable to reduce to a low level or substantially eliminate habituation of the brain, and therefore the term "random" as used herein is intended to mean a pattern which is sufficiently variable for this purpose. It should also be understood that the switching should be at intervals which are sufficiently short that substantial habituation does not occur, but the intervals must not be too short or they will be ignored by the brain. Since habituation commonly occurs after between about 2 and 20 seconds (depending on the individual), switching of the signal from one pad to another after between 5 and 20 seconds has been found to be suitable in most cases. The circuit shown is sufficiently random that the signal may occasionally be applied to the same pad twice in succession. In some cases the switching interval can be as short as one second or as high as 30 seconds or more, and in a few instances the switching interval can be as high as 600 seconds, although this is not preferred.

It will be appreciated that if desired, signal can be applied to more than one skin pad at a time. For example, two of the relay contacts 30-1 to 30-6 and two of the channel selector transistors Q1 to Q6 may be operated at any given time, to apply signal to two pads at a time. This may be achieved by using a counter 70 which counts in pairs, or by employing two counters 70.

Figure 5:
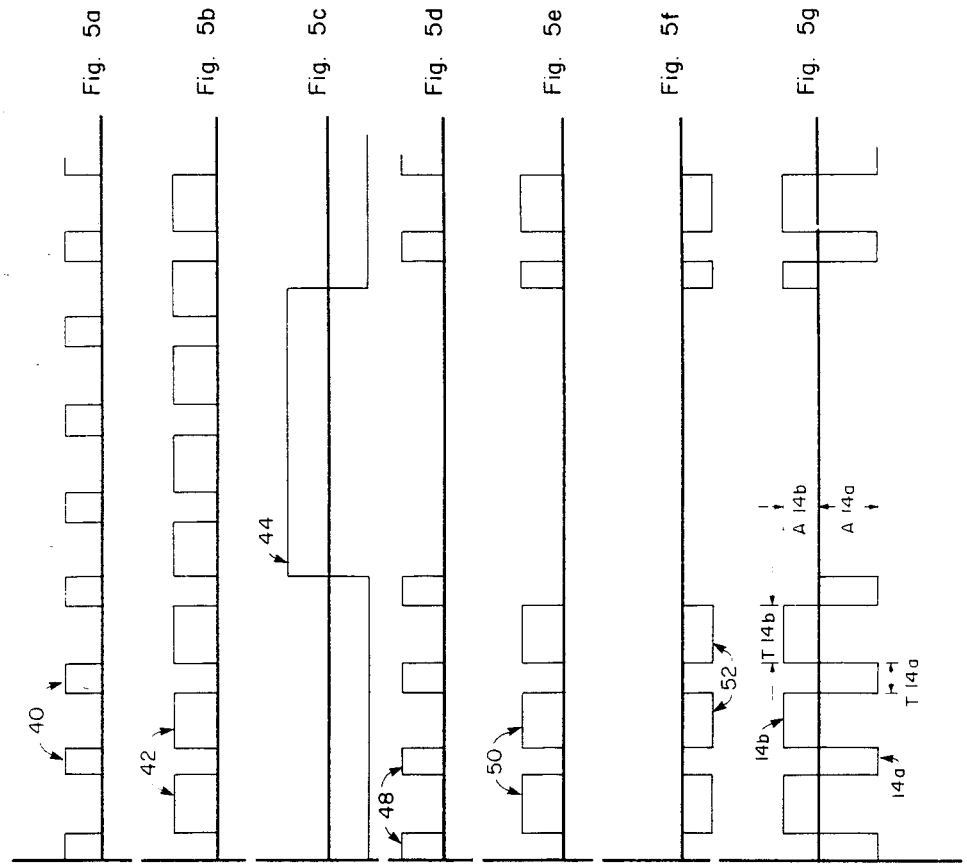
FIG. 5 is a drawing showing various wave forms for the pulse generator of FIG. 4.

It will be seen that the FIG. 5 circuit includes a selector switch 82 containing terminals 84-1 to 84-6 and a seventh terminal 84-7 marked as "random". Terminals 84-1 to 84-6 are connected directly to the cathodes of diodes D25 to D30 so that when the movable switch contact 86 is connected directly to any of the terminals 84-1 to 84-6, a positive voltage is applied directly to the base of a selected transistor Q11 to Q16 respectively, operating a selected relay and field effect transistor Q1 to Q6 to apply the pulse train 14 to a desired pad. When the switch contact is connected to terminal 84-7, +9 volts is applied to the variable frequency oscillator 68, the counter 70, and the multivibrator 80, producing random channel selection.

If desired, the apparatus shown can be equipped with means for applying a very small negative DC current, either pulsed or of constant level (the term "DC" or "direct current" is intended to include both constant and pulsed current of single polarity) to a desired location on a user's body in place of the pulse train 14 described. It is found that a very small DC current, of between 5 and 10 microamperes, can improve regeneration of nerves and other tissue after damage. This current is substantially smaller than the current normally used for acupuncture.

For this purpose switch contact 88 is provided as shown in FIG. 6, movable between the terminal 90 which is the normal position for acupuncture, and terminal 92 in which the current flows through a fixed resistor R99 and a variable resistor VR100. The variable resistor VR100 is of value such that the current can be reduced to approximately 0.1 to 10 microampere pulses. The pulses can be bi-polar as provided by the pulse generator circuit 12 described, or alternatively the bias can be turned off by switch 94 shown in dotted lines in FIG. 4. Alternatively, pure DC current (which is preferred for nerve and tissue regeneration) can be supplied by leaving switch contact 88 on terminal 90 and turning off the pulse train 14 (e.g. by opening a switch, not shown, in the circuit to terminal 20). Variable resistor VR12 can then be adjusted to set the output of circuit 56 at between 0 and ±50 microamperes.

Figure 8:
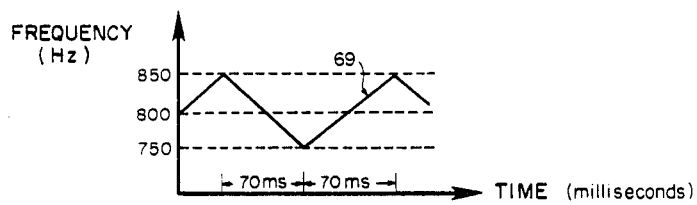
FIG. 8 is a plot showing the variation of frequency with time of a variable frequency oscillator in the FIG. 7 circuit.

The apparatus shown lends itself to use with biofeedback, in which the user observes a particular parameter, such as his pulse rate, or the wave form of his electrocardiogram, or his blood pressure, or his skin resistance, or the form of certain brain waves, and adjusts the acupuncture pulse train frequencies and current in an attempt to influence these parameters. A block diagram for such an arrangement is shown in FIG. 8. As shown, the apparatus 10 of the invention is connected to a user indicated at 100. Contacts 102 connected to the user are connected to a measurement device 104 which measures a parameter such as the user's electrocardiogram. The measurement device 104 is connected to a comparator 106, which is also connected to a storage device 108 containing a representation of a "normal" electrocardiogram. Each electrocardiogram is subjected to Fourier analysis in the comparator 106 (e.g. three or four major peaks are selected), and the difference between the actual and observed electrocardiograms is used to drive the apparatus of the invention in an attempt to reduce the difference between the two. Alternatively the comparator 106 can simply be a dual beam oscilliscope, with the "normal" electrocardiogram displayed with one beam and the observed electrocardiogram displayed by the other beam, so that the user himself can attempt to match the two as closely as possible. The same approach may be used for other parameters such as those mentioned.

Although the description has referred to the signal applied to the user as an electrical acupuncture signal, such signal can if desired be a different type of signal, e.g. a different electrical stimulating signal or a non-electrical signal, e.g. an optical signal, a thermal signal, or a radiation signal. Where the signal is used for transcutaneous nerve stimulation, it may be precisely the same signal as the acupuncture signal described, except that instead of being applied to acupuncture points, it is applied to different points on the body, to relieve pain.

We claim:
1. Electrotherapy apparatus comprising:
(a) means for providing an electrical stimulating signal,
(b) at least three channels each for receiving said signal,
(c) at least three signal application means one connected to each channel and each adapted to apply said signal to a different location on a user,
(d) means for randomly switching said signal among said channels thus to switch said signal randomly from one location to another on said user, to reduce habituation of the brain of said user,
(e) and means associated with at least one of said means (a) and (b) for separately adjusting the intensity of the signal applied to each invividual signal application means to a selected constant intensity at such signal application means.

2. Apparatus according to claim 1 wherein said means for random switching includes means for applying said signal to each said channel for a period of at least about one second.

3. Apparatus according to claim 2 wherein said means for random switching includes means for varying said period between about one and thirty seconds.

4. Apparatus according to claim 2 wherein said means for random switching includes means for varying said period between about one and six hundred seconds.

5. Apparatus according to claim 1 wherein said means for random switching includes means for providing an interval between applications of said stimulating signal in which no said signal is applied to any of the channels.

6. Apparatus according to claim 1 wherein said number of channels and said number of signal application means is each at least five.

7. Apparatus according to claim 1 wherein said number of channels and said number of signal application means is each at least six.

8. Apparatus according to claim 1 wherein said means (a) for providing said electrical stimulating signal includes generating means for generating said signal in the form of a bi-polar signal comprising negative stimulating pulses separated by positive bias pulses, the integral of said signal being substantially zero.

9. Apparatus according to claim 8 wherein said means for adjusting comprises means for adjusting the length of said bias pulses and further includes means for automatically adjusting the amplitude of said bias pulses inversely with the duration of said bias pulses, so that the integral of said signal remains substantially zero during said adjustment.

10. Apparatus according to claim 9 wherein said means for adjusting includes means for adjusting the amplitude of said signal applied to each signal application means.

11. Apparatus according to claim 1 wherein said means for randomly switching comprises a set of selector switches one for each channel and each operable to cause application of said signal to its associated channel, first and second oscillator means, counting means coupled to said second oscillator means and driven thereby, said first oscillator means being a variable frequency oscillator, and means connected to said first oscillator means and to said counting means and to said selector switches for activating one of said selector switches upon occurrence of a selected state of said second oscillator means.

12. Apparatus according to claim 1 and including a set of electroconductive pads, one pad for each channel, and fastening means secured to each pad to hold such pad firmly against a user's skin.

13. Apparatus according to claim 1 wherein said means for producing said signal includes a constant current source for maintaining the current of said signal substantially constant.

14. Apparatus according to claim 1 wherein said signal consists of negative pulses of a repetition rate of between 100 and 500 Hz, arranged in groups having a repetition rate of between 1 and 50 Hz.

15. Apparatus for applying a stimulating signal to a user comprising:
(a) means for providing said stimulating signal,
(b) at least three channels each for receiving said signal,
(c) at least three signal application means one connected to each channel and each adapted to apply said signal to a different location on a user,
(d) means for randomly switching said signal among said channels thus to switch said signal randomly from one location to another on said user, to reduce habituation of the brain of said user,
(e) and means associated with at least one of said means (a) and (b) for separately adjusting the intensity of the signal applied to each individual signal application means to a selected constant intensity at such signal application means.

16. Apparatus according to claim 15 wherein said means for random switching includes means for providing an interval between applications of said stimulating signal in which no said stimulating signal is applied to any of the channels.

17. A method of applying an electrical stimulating signal to a user, comprising: (a) generating said electrical stimulating signal, (b) providing at least three channels each for applying said signal to a different location on said user, and (c) randomly switching said signal among said channels thus randomly to switch said signal among said locations on said user to reduce habituation of the brain of said user.

18. The method according to claim 17 wherein in said step (c) said signal is applied to each said channel for a period greater than one second.

19. The method according to claim 18 wherein in said step (c) said signal is applied to each said channel for a period of between about one and thirty seconds.

20. The method according to claim 17 wherein in said step (c) a rest interval is provided between applications of said signal to said channels, in which no said signal is applied to any of said channels.

21. The method according to claim 17 wherein the number of said channels is at least five.

22. The method according to claim 17 wherein the number of said channels is at least six.

23. The method according to claim 17 wherein in said step (a) said signal is generated as a bi-polar signal comprising negative stimulating pulses separated by positive bias pulses, the integral of said signal being substantially zero.

24. The method according to claim 23 wherein said negative pulses have a repetition rate of about 100 and 500 Hz and are arranged in groups having a repetition rate of between 1 and 20 Hz.

25. The method according to claim 23 wherein said negative pulses are each of constant pulse width and said method includes the step of adjusting separately the amplitude of said signal applied to each said location.

26. A method of applying a stimulating signal to a user, comprising: (a) generating said stimulating signal, (b) providing at least three channels each for applying said signal to a different location on said user, and (c) randomly switching said signal among said channels thus randomly to switch said signal among said locations on said user to reduce habituation to the brain of said user.

27. The method according to claim 26 wherein a rest interval is provided between applications of said signal to said channels, in which no said signal is applied to any of said channels.

28. Electrostimulating apparatus comprising:
(a) means for providing a transcutaneous nerve stimulation signal,
(b) at least three channels each for receiving said signal,
(c) at least three signal application means one connected to each channel and each adapted to apply said signal to a different location on a user,
(d) means for randomly switching said signal among said channels thus to switch said signal randomly from one location to another on said user, to reduce habituation of the brain of said user,
(e) and means associated with at least one of said means (a) and (b) for separately adjusting the intensity of the signal applied to each individual signal application means.

* * * * *